US006410002B2

(12) United States Patent
Scafidi et al.

(10) Patent No.: US 6,410,002 B2
(45) Date of Patent: *Jun. 25, 2002

(54) PREPARATION OF ANTIPERSPIRANT GELS WHICH OBVIATES THE USE OF SIMPLE GLYCOLS

(75) Inventors: Anthony Aloysius Scafidi, Westchester; Zhuning Ma, Schaumburg; David Allen Brewster, Buffalo Grove, all of IL (US)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/853,347

(22) Filed: May 11, 2001

Related U.S. Application Data

(60) Provisional application No. 60/204,060, filed on May 12, 2000.

(51) Int. Cl.$^7$ .............................. A61K 7/32; A61K 7/34; A61K 7/38; A61K 7/00
(52) U.S. Cl. ........................... 424/65; 424/66; 424/400; 424/401
(58) Field of Search .............................. 424/65, 66, 68, 424/400, 401

(56) References Cited

U.S. PATENT DOCUMENTS

| 4,673,570 | A | * | 6/1987 | Solati et al. |
| 4,944,938 | A | * | 7/1990 | Potini et al. |
| 5,066,756 | A | * | 11/1991 | Raleigh et al. |
| 5,393,518 | A | * | 2/1995 | Kwass |
| 5,433,943 | A | * | 7/1995 | Osipow et al. |
| 5,534,245 | A | * | 7/1996 | Galleguillos et al. |
| 5,587,153 | A | * | 12/1996 | Angelone, Jr. et al. |
| 5,718,890 | A | * | 2/1998 | Putnam et al. |
| 5,811,487 | A | * | 9/1998 | Schulz, Jr. et al. |
| 5,843,414 | A | * | 12/1998 | Hilvert et al. |
| 5,863,525 | A | * | 1/1999 | Angelone, Jr. et al. |
| 5,925,338 | A | * | 7/1999 | Karassik et al. |

FOREIGN PATENT DOCUMENTS

| WO | 92/05767 | 4/1992 |
| WO | 97/06777 | 2/1997 |
| WO | 98/43605 | 10/1998 |

OTHER PUBLICATIONS

PCT International Search Report in a PCT application PCT/EP 01/05122.

* cited by examiner

Primary Examiner—Shelley A. Dodson
(74) Attorney, Agent, or Firm—Kevin J. Stein

(57) ABSTRACT

A clear emulsion and gel-type cosmetic composition, and in particular to an antiperspirant and/or deodorant composition which comprises a water-in-oil emulsion comprising:

a) about 65% to about 75% of an aqueous solution of an effective amount of antiperspirant active;

b) about 25% to about 35% of an oil phase consisting of silicones, emollients and a silicone emulsifying agent, and comprising at least one volatile silicone, at least one non-volatile ester or at least one nonvolatile silicone, and wherein at least one oil phase soluble ingredient has a refractive index of about 1.40 to about 1.45;

c) about 0.01 to about 8.5% of a coupling agent; and d) at least one polymeric ethylene oxide glycol adduct which component raises the refractive index of said aqueous solution, and optionally another water soluble, non-simple glycol component which raises the refractive index of said aqueous solution;

wherein said composition is essentially free of glycols and low and middle chain alcohols;
is described.

4 Claims, No Drawings

PREPARATION OF ANTIPERSPIRANT GELS WHICH OBVIATES THE USE OF SIMPLE GLYCOLS

This application claims priority from Provisional application Ser. No. 60/204,060, filed May 12, 2000.

BACKGROUND OF THE INVENTION

Cosmetic products can be in emulsion form. Antiperspirant and deodorant products which are in emulsion form are known in the art. These products may have an oil phase and a water phase. Moreover, these emulsions may be in gel form.

One can use such gel-type products, which can be antiperspirant and deodorants, by rubbing the underarm area of the body so as to apply an odor and/or perspiration reducing layer of the gel to the skin. Because such products are applied directly to the skin, such products should have certain aesthetic properties so that they will achieve consumer acceptance. Included in such aesthetic properties are non-tackiness during dry-down, non-tackiness when the user perspires after application of the product, smoothness, glide, a lack of oily or crumbly or scratchy feeling; and a product which leaves no white physical residue on skin or clothes after application.

Clarity is also an especially desired esthetic property in the eyes of the consumer.

It is an object of this invention to provide emulsion and gel-type cosmetic products especially an antiperspirant or deodorant product which has the above-recited aesthetic properties.

The following patent publications relate to this field of invention.

U.S. Pat. No. 5,587,153 discloses a clear gel-type cosmetic product which has a viscosity of at least about 50,000 cps at 21° C., and includes an emulsion with an oil phase and a water phase that includes an incorporated active ingredients. The refractive indices of the water and oil phases match to at least 0.0004, the refractive index of the product is about 1,4000, and the product clarity is better than thirty NTU.

U.S. Pat. No. 5,863,525 also discloses a clear gel-type cosmetic product which has a viscosity of at least about 50,000 cps at 21°C., and includes an emulsion with an oil phase and a water phase that includes an incorporated active ingredient. The refractived indices of the water and oil phases match to at least 0.0004 the refractive index of the product is about 1,4000, and the product clarity is better than thirty NTU.

U.S. Pat. No. 5,925,338 discloses a clear gel composition comprising a water-in-oil emulsion of specified viscosity, and specified amounts of water and oil, wherein the oil phase comprises a volatile cyclic silicone, an emulsifying agent, optionally a non-volatile oil, and a volatile linear silicone.

U.S. Pat. No. 5,393,518 discloses an optically clear antiperspirant product in the form of a stable water-in-oil emulsion with a specified viscosity which includes a stabilizing agent that has substantial solubility in each of the oil and water phases and which has long term stability over specified temperature ranges.

U.S. Pat. No. 6,007,799 discloses a clear cosmetic gel composition in the form of a water-in-oil emulsion, and methods of forming and using the composition.

WO 92/05767 discloses a clear gel-type cosmetic product that has a viscosity of at least about 50,000 cps at 21 degrees C., and includes an emulsion with an oil phase and a water phase, wherein the refractive indices of the water and oil phases match to at least 0.0004, the refractive index of the product is about 1.4000 and the product clarity is better than 30 NTU.

SUMMARY OF THE INVENTION

The invention relates to a clear emulsion and gel-type cosmetic composition, and in particular to an antiperspirant and/or deodorant composition which comprises a water-in-oil emulsion comprising:

a) about 65% to about 75% of an aqueous solution of an effective amount of antiperspirant active;

b) about 25% to about 35% of an oil phase consisting of silicones, emollients and a silicone emulsifying agent, and comprising at least one volatile silicone, at least one non-volatile ester or at least one nonvolatile silicone, and wherein at least one oil phase soluble ingredient has a refractive index of about 1.40 to about 1.50;

c) about 0.01 to about 8.5% of a coupling agent; and d) at least one polymeric ethylene oxide glycol adduct which component raises the refractive index of said aqueous solution, and optionally another water soluble, non-simple glycol component which raises the refractive index of said aqueous solution;

wherein said composition is essentially free of glycols and low and middle chain alcohols.

As noted just above, the water phase is essentially free of glycols and low and middle chain alcohols and incorporates polyethylene glycols, inorganic salts, organic salts, amino acids or urea to raise the refractive index of the aqueous phase. Simple glycols are defined herein as alkanes and alkoxyalkanes containing at least two hydroxy groups and three or less carbon atoms. Propylene glycol is a non-limiting examples of a simple glycol. Complex or non-simple glycols are polymeric ethylene oxide glycol adducts which are described below. Low chain alcohols have from one to four carbon atoms. Middle chain alcohols have from 5 to 12 carbon atoms. Propylene glycol and dipropylene glycol are non-limiting examples of glycols. Low chain alcohols have from one to four carbon atoms. Middle chain alcohols have from 5 to 12 carbon atoms.

Complex or non-simple glycols are polymeric ethylene oxide glycol adducts which are included in compositions of the invention, can be Carbowaxes which are a family of linear polymers formed by the addition reaction of ethylene oxide with glycol. The generalized formula for polyethylene glycol is:

HO—(CH$_2$CH$_2$O)$_n$—H  Formula I

Also included within polyethylene glycols are methoxy polyethylene glycols which have the formula:

CH$_3$—O—(CH$_2$CH$_2$O)$_n$—H  Formula II

Each polyethylene glycol is designated by a number that represents its average molecular weight. For example, Carbowax Peg 600 corresponds to an average number of repeating oxyethylene groups ("n") of 13. polyethylene glycols are polymeric glycols with an "n" value from 2–33 for polyethylene glycols (formula I above) which represents a molecular weight range of 106–1460. polyethylene glycols are also the methoxy adducts described above. With regard to the methoxy adducts (formula II above), polyethylene glycols have "n" values of 4–18 representing, a molecular weight range of 208–824.

The invention also relates to a method for preventing and controlling perspiration wetness in humans which comprises applying to the underarm area an effective amount of a composition of the invention.

DETAILED DESCRIPTION OF THE INVENTION

As used herein, % means weight % of the entire composition, unless otherwise specified. As used herein "essentially free of glycols" means that the level of glycols present in the composition is in too low off amount to contribute to the tackiness or the stickiness or the wetness or the coolness of the product either during dry down or on perspiring after the product has been applied. This level is usually 0 to about 1% glycols or less. "Essentially free of low or middle chain alcohols" means that the level of low or middle chain alcohols present is so low that those low or middle chain alcohols in too low off amount to contribute to the tackiness or the stickiness of the product either during dry down or on perspiring after the product has been applied. This level is usually about 0 to about 1% of low and/or middle chain alcohols.

All of the ingredients used to prepare compositions of the invention are known or can be prepared according to known methods. The compositions of the invention can be prepared by known methods or by methods analogous to known methods.

The invention relates to a clear emulsion and gel-type cosmetic composition, and in particular to an antiperspirant and/or deodorant composition which comprises a water-in-oil emulsion comprising:
  a) about 65% to about 75% of an aqueous solution of an effective amount of antiperspirant active;
  b) about 25% to about 35% of an oil phase consisting of silicones, emollients and a silicone emulsifying agent, and comprising at least one volatile silicone, at least one non-volatile ester or at least one nonvolatile silicone, and wherein at least one oil phase soluble ingredient has a refractive index of about 1.40 to about 1.50 or more preferably about 1.40 to about 1.45;
  c) about 0.01 to about 8.5% of a coupling agent; and
  d) at least one polymeric ethylene oxide glycol adduct which component raises the refractive index of said aqueous solution, and optionally another water soluble, non-simple glycol component which raises the refractive index of said aqueous solution;
wherein said composition is essentially free of glycols and low and middle chain alcohols.

The water phase is essentially free of glycols and low and middle chain alcohols and incorporates polyethylene glycols, inorganic salts, organic salts, amino acids or urea to raise the refractive index of the aqueous phase. Glycols are defined here as alkanes and alkoxyalkanes containing at least two hydroxy groups. Propylene glycol and dipropylene glycol are non-limiting examples of glycols. Low chain alcohols have from one to four carbon atoms. Middle chain alcohols have from 5 to 12 carbon atoms. Propylene glycol and dipropylene glycol are non-limiting examples of glycols. Low chain alcohols have from one to four carbon atoms. Middle chain alcohols have from 5 to 12 carbon atoms.

The water phase is essentially free of glycols and low and middle chain alcohols and incorporates polyethylene glycols, inorganic salts, organic salts, amino acids or urea to raise the refractive index of the aqueous phase The water phase incorporates polyethylene glycols, inorganic salts, organic salts, amino acids or urea to raise the refractive index of the aqueous phase.

The invention also relates to a composition as described above wherein the refractive indices of the water phase and the oil phase are matched to within about 0.0008, or more preferably about 0.0004. The invention also relates to a composition as described above wherein the refractive index of the final composition is about 1.4090 to about 1.4200. The invention also relates to a composition as described above which contains dimethicones and substituted dimethicones. The invention also relates to a composition as described above which contains silicone copolyol as and emulsifying agent. The invention also relates to a composition as described above which contains a silicone elastomer such as DC 9040 or DC9010.

The invention also relates to optically clear compositions which have an NTU of 50 or lower. NTU means Nephelometric Turbidity Units.

The invention also relates to cosmetic compositions as described above which have decreased tackiness, stickiness, wetness and coolness measurements as ascertained by trained sensory panelists.

As noted above, the compositions of the invention can have an aqueous phase from about 65% to about 75%. The compositions of the invention can have an oil phase of about 25% to about 35%.

The antiperspirant active ingredient can be present at about 5 to about 50%.

As noted just above, the compositions of the invention can have an optical clarity of 50 NTU or lower. More preferably, they can have an optical clarity of about 0 to about 30 NTU.

The invention also relates to a method for preventing and controlling perspiration wetness in humans which comprises applying to the underarm area an effective amount of a composition of the invention.

What follows now is a more detailed description of the ingredients which are included in the compositions of the invention.

As has been noted above, the compositions of the invention are essentially free of glycols and low to middle chain alcohols. However, glycols normally are used in gelled cosmetic compositions to raise the refractive index of the water phase and thereby match the refractive index of the water phase to the refractive index of the oil phase and thereby obtain a clear composition.

Without simple glycols, another means must be found to raise the refractive index of the water phase of the composition.

In the present invention, this is accomplished by using inclusions other than simple glycols in the water phase. More specifically, said deodorant or antiperspirant active can have this refractive index raised by combining it with a non-simple glycol compound that is water soluble, and raises the refractive index of the water phase and is not deleterious to the properties of the antiperspirant or deodorant active, or to the esthetics of the final composition. Such compounds are preferably are polymeric ethylene oxide glycol adducts as described herein. Such compounds may also be compounds which have a carboxylate group. Preferably such compounds can include an amino acid such as glycine, alanine or dl-trytophan. Alternatively other inorganic salts such as water soluble salts or more preferably monovalent, divalent, trivalent salts including sodium chloride, sodium sulfate, calcium chloride, calcium sulfate, magnesium chloride, aluminum salts and mixtures thereof can be added to the water phase to raise the refractive index thereof. Other examples include salts of organic acids such as sodium lactate, acetamide MEA and lactamide MEA. Also urea and other salts of amino acids may be utilized such as zinc glycinate.

Such inclusions may be mixtures of all of the compounds set forth just above.

An advantage to using this method for matching refractive indices is that it achieves compositions that are not sticky or tacky during drydown or after the user has re-perspired. Another advantage is that this represents an inexpensive way to obtain clear compositions.

Deodorant or antiperspirant actives

Nonlimiting examples of said deodorant or antiperspirant actives which have been combined with the just above mentioned compounds are as follows: antiperspirant complexes using the antiperspirant salts which are known in the art. For example, 3,792,068 Luedders et al., herein incorporated by reference, discloses complexes of aluminum, zirconium and amino acids such as glycines. Complexes such as those disclosed in Luedders and other similar complexes are commonly known as ZAG( OR Zag). ZAG complexes are chemically analyzable for the presence of aluminum, activated ZAG compounds and chlorine. ZAG complexes useful herein are identified by the specification of both the molar ratio of aluminum to zirconium (the Al:Zr ratio) and the molar ratio of total metal to chlorine (metal:Cl) ZAG complexes useful herein have an Al:Zr ratio of from about 1.67 to about 12.5 and a metal:Cl ratio of about 0.73 to about 1.93.

Another patent which discloses ZAG compounds is U.S. Pat. No. 4,985,238 to Tanner et al. This just-mentioned patent is herein incorporated by reference. Preferred ZAG complexes are described in U.S. Pat. No. 4,985,238 to Tanner et al.

Water

The water which is used in the aqueous phase of compositions of the invention can be deionized water.

The oil phase

The oil phase of compositions of the invention can be a blend of liquids which include a polyorganosiloxane, such as DC9010, DC9040 or more preferably dimethicone or cyclomethicone, such as DC 245 or DC345. Dimethicone is available from Dow Corning under the name DC-225and DC200 fluid and it has a refractive index of about 1.3995. Other non-silicone liquids which can be included in the oil phase of nonlimiting of compositions of the invention include, isopropyl myristate, isopropyl palmitate, and diisopropyl sebacate. These have refractive indices respectively of 1.4340, 1.4370, and 1.4320. Other non-limiting, non-silicone oils which can be included in the oil phase of the compositions of the invention include C12–15 alcohols benzoate, isostearyl isostearate, octyl dodecanol, octyl nonanoate and PPG-14 butyl ether.

The oil phase of the compositions of the invention can also include a silicone emulsifying agent at a level that is effective to form emulsions. Non-limiting examples of silicone emulsifying agents include Abil EM90, Abil EM97, DC9010 silicone elastomer, and most preferably a polyether substituted silicone of cyclomethicone and dimethicone copolyl which can be obtained form Dow Corning under the name DC-3225C and DC-5225C. This emulsifying agent is a dispersion of dimethicone copolyol, which is a silicone surfactant in cyclomethicone (Dow Corning 344 fluid). The dimethicone is present at about 10% of the dispersion, and the cyclomethicone is present at about 90% of the dispersion. Stable emulsions containing a large percentage of oil phase can be prepared using this emulsifying agent. The oil phase of the compositions of the invention can also contain organic esters such as isostearyl stearate, Finsolv TN C12–C15 benzoates, ethers such as polyethylene glycols, PPG 14 Butyl Ether, hydrocarbons such as Silkflo 366 and 344 Permethyl 102A isostearyl cyclohexane and halo carbons such as chlorocarbons or fluorocarbons.

Coupling agent

Compositions of the invention include a coupling agent. Such coupling agent is illustratively (but not limited to) the following:

Ethylene carbonate

N-methylglucamine

Linear ethoxylated polymer of methanol

Ethylene glycol monoethyl ether

Diethylene glycol monoethyl ether

Propoxylated oleyl alcohol

Butyl stearate

Butyl myristate

Mineral Spirits

PPG (2–8) myristyl ether

PPG (2–8) lauryl ether

Sorbitol

PPG (2–10) cetyl ether

PEG-6 diisopropyl adipate

Methoxy PEG-22 dodecyl-glycol copolymer

PEG-30 Glyceryl monoacetate sorbitol

PEG-3 oleyl ether phosphate

PEG-(2–5) oleyl ether

PPG-(2–5) lanolate

PPG-(2–8) isostearate

Propylene glycol (2) methyl ether

PPG-(2–3) methyl ether

PPG-14 butyl ether

Ethoxylated (2–20 moles) glucose

Propoxylated (2–20 moles) glucose

PPG-15 Stearyl ether

PPG-(5–20) methyl glucose ether

Propylene carbonate

Glycerine

This coupling agent acts to stabilize the emulsion and also acts as a clarifying agent. Moreover, various of these coupling agents, aid in drying and has a cooling effect, providing advantageous aesthetic properties for the composition.

The coupling agent can be one compound or a mixture of compounds.

Illustratively, the coupling agent is present in an amount of from about 0.01% to about 8.5% by weight, preferably from about 0.5% to about 8.5% by weight, of the total weight of the composition.

Optional Ingredients

Compositions of the invention can further comprise other cosmetic ingredients such as fragrances, colorants, emollients, preservatives, and thickeners.

Optically clear compositions using ingredients described above can be achieved by matching the refractive index of the oil phase with the refractive index of the water phase. This is done by combining the ingredients of the oil phase and measuring the refractive index of the resulting oil phase, at about room temperature, which is about 21° C. Then the ingredients which comprise the aqueous phase are mixed and its refractive index is measured at room temperature, 21° C.

If necessary, in order to match the refractive index of the water phase to that of the oil phase, water can be added to the water phase (to lower total water phase refractive index) In order to raise water phase refractive index, the level of the water soluble salt, amino acid or other non-glycol, water soluble additive such as urea may be added for adjustment purposes.

Following this adjustment, the water phase is optically remeasured to determine whether its refractive index matches that of the oil phase. Thus, if the oil phase had a refractive index of 1.4100 and the initial refractive index of the water phase was 1.3980, additional non-glycol inclusions such as an inorganic salt are added to make its refractive index about 1.4100. In the compositions of the invention, the closer the match of the water and the oil phase, the more optically clear is the resulting emulsion.

The above oil phase and water phase refractive indices are measured by using refractometers which are known in the art. An example of such a refractometer is a Reichert-Jung, Abbe Mark II Refractometer Model 10480. And the refractive index is measured at a suitable temperature, usually, at about 21° C. which is room temperature.

The water phase is then added slowly to the oil phase, while the mixture is mixed at about 10,000 RPM or higher as needed to form a stable emulsion. A sonolator is the preferred method of shearing the product to form a gel with a viscosity of 50,000–200,000 cps. at about 21° C measured using a Brookfield Viscometer with a T-F bar @10 rpm/30 seconds. Preferably the emulsion has a viscosity between about 50,000 cps to about 100,000 cps measured as described above.

Within the oil phase there is a volatile silicone. The volatile silicone can range from about 1% to about 5%, more preferably between about 2% to about 4%.

Within the oil phase there is a non-volatile silicone or a non-volatile ester. The non-volatile silicone or non-volatile ester can range from about 9% to about 25%, more preferably between about 15% to about 25%. The non-volatile silicone or non-volatile ester can serve as emollients in compositions of the invention. The emollient can range from about 0.5% to about 5%, more preferably between about 2% to about 4%.

Compositions of the invention can be made by known processes or by processes which are analogous to known processes. What follows are specific compositions of the invention which are clear gels and which have been made. These examples are illustrative and are not meant to limit the present invention.

EXAMPLE 1

| INGREDIENT | WEIGHT % |
|---|---|
| DIMETHICONE 350 VISCOSITY | 15.8 |
| WATER, SOFT | 7.5 |
| CARBOWAX 400 | 8.5 |
| AZG-442 SOLUTION | 56.0 |
| DRAGOCO 0/724869 | 0.8 |
| CYCLOMETHICONE AND DIMETHICONE COPOLYOL | 7.4 |
| SILICONE FLUID 556 | 4.0 |
| TOTAL | 100 |

EXAMPLE 2

| INGREDIENT | WEIGHT % |
|---|---|
| DIMETHICONE 350 VISCOSITY | 8.0 |
| CYCLOMETHICONE(AND) DIMETHICONE CROSSPOLYMER | 2.0 |
| SILICONE SF 1555 | 4.0 |
| UREA | 4.3 |
| WATER, SOFT | 7.9 |
| CARBOWAX 400 | 4.0 |
| WESTCHLOR ZR 41, 45% | 56.0 |
| FRAGRANCE | 0.8 |
| CYCLOMETHICONE AND DIMETHICONE COPOLYOL | 3.5 |
| CYCLOPENTASILOXANE | 9.15 |
| CETYL DIMETHICONE COPOLYOL | 0.35 |

EXAMPLE 3

| INGREDIENT | WEIGHT % |
|---|---|
| DIMETHICONE 350 VISCOSITY | 21.7 |
| WATER, SOFT | 5.5 |
| CARBOWAX 400 | 8.5 |
| Azg-442 | 56.0 |
| FRAGRANCE | 0.8 |
| CETYL DIMETHICONE COPOLYOL | 2.5 |
| SILICONE FLUID SF-1555 | 3.5 |
| UREA | 1.5 |

EXAMPLE 4

| INGREDIENT | WEIGHT % |
|---|---|
| DIMETHICONE 350 VISCOSITY | 8.0 |
| 9040 SILICONE ELASTOMER BLEND | 2.0 |
| SILICONE SF 1555 | 4.0 |
| UREA | 0.5 |
| WATER, SOFT | 7.2 |
| CARBOWAX 400 | 8.0 |
| WESTCHLOR ZR 41, 45% | 56.0 |
| FRAGRANCE | 0.8 |
| CETYL DIMETHICONE COPOLYOL | 1.0 |
| CYCLOPENTASILOXANE | 12.00 |

A composition of the invention can be made by preparing the oil phase and the water phase in separate vessels and matching their respective refractive indices. The water phase is added gradually to the oil phase with rapid agitation using a lightning mixer. The resulting mixed solution is then placed in a homogenizer and mixed at 10,000 rpm or higher until it gels.

Moreover, the above compositions have reduced tackiness or stickiness, reduces wetness and coolness. This can be demonstrated by trained sensory panelists applying measured doses of the product to underarms and inner forearms and evaluating tackiness immediately after application, and again at 5, 10 and 15 minute intervals. The panelists can also evaluate wetness and coolness.

While particular embodiments of the invention have been shown and described, various modifications will be apparent to those skilled in the art, and therefore it is not intended that the invention be limited to the disclosed embodiments or the details thereof, and departures may be made therefrom within the spirit and the scope of the inventions.

What is claimed is:

1. A clear emulsion and gel cosmetic composition which is an antiperspirant and/or deodorant composition which comprises a water-in-oil emulsion comprising:
   a) about 65% to about 75% of an aqueous solution of an effective amount of antiperspirant active;
   b) about 25% to about 35% of an oil phase consisting of silicones, emollients and a silicone emulsifying agent, and comprising at least one volatile silicone, at least one non-volatile ester or at least one nonvolatile silicone, and wherein at least one oil phase soluble ingredient has a refractive index of about 1.40 to about 1.45;
   c) about 0.01 to about 8.5% of a coupling agent; and
   d) at least one polymeric ethylene oxide glycol adduct which component raises the refractive index of said aqueous solution, and optionally another water soluble, non-simple glycol component which raises the refractive index of said aqueous solution;

wherein said composition is essentially free of glycols and low and middle chain alcohols.

2. A composition according to claim 1, wherein said non-simple glycol is selected from the group consisting of glycine, alanine, dl-trytophan; divalent, trivalent salts including sodium chloride, sodium sulfate, calcium chloride, calcium sulfate, magnesium chloride, aluminum salts, aluminum lactate, zirconium lactate, sodium lactate, acetamide MEA and lactamide MEA, urea zinc glycinate, and mixtures thereof.

3. A composition according to claim 1, wherein the refractive index of the said final composition is about 1.4095 to about 1.4200.

4. A composition according to claim 1, wherein the at least one oil phase soluble ingredient has a refractive index of about 1.40 to about 1.45.

* * * * *